United States Patent [19]

Pallos

[11] 4,056,627
[45] Nov. 1, 1977

[54] BIS-CYCLOALKYLTHIOCARBAMATES AS INSECT CONTROL AGENTS

[75] Inventor: Ferenc M. Pallos, Walnut Creek, Calif.

[73] Assignee: Stauffer Chemical Company, Westport, Conn.

[21] Appl. No.: 666,296

[22] Filed: Mar. 10, 1976

Related U.S. Application Data

[62] Division of Ser. No. 574,472, May 5, 1975, Pat. No. 3,960,917.

[51] Int. Cl.² .......................... A01N 9/12; A01N 9/20
[52] U.S. Cl. .............................. 424/300; 424/DIG. 12
[58] Field of Search ....................... 424/300, DIG. 12; 260/455 A

[56] References Cited

U.S. PATENT DOCUMENTS 3,846,466   11/1974   Pallos ............................... 260/455 A
3,960,917   6/1976   Pallos ............................... 260/455 A

*Primary Examiner*—V. D. Turner
*Attorney, Agent, or Firm*—Joel G. Ackerman

[57] ABSTRACT

Compounds having the formula

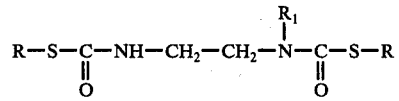

in which R is a cycloalkyl group having from 3 to 7 carbon atoms, and $R_1$ is lower alkyl. The compounds are selectively useful in controlling insects.

6 Claims, No Drawings

BIS-CYCLOALKYLTHIOCARBAMATES AS INSECT CONTROL AGENTS

This is a division of application Ser. No. 574,472, filed May 5, 1975, now U.S. Pat. No. 3,960,917.

DESCRIPTION OF THE INVENTION

This invention relates to certain novel chemical compounds effective in combatting certain noxious insects. More particularly, this invention relates to bis-cycloalkylthiocarbamates having the formula

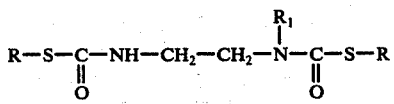

in which R is a cycloalkyl group having from 3 to 7 carbon atoms, and $R_1$ is lower alkyl, preferably alkyl having from 1 to 4 carbon atoms. For instance, R may be cyclopropyl, cyclobutyl, cyclopentyl, cyclohexyl, cycloheptyl, etc., and $R_1$ may be methyl, ethyl, isopropyl, n-propyl, n-butyl, and the like. These compounds have been found to have utility in combatting certain insects in that they exert a disrupting influence upon the normal development of these insects. That is, they impede the metamorphosis of larvae to pupae and/or pupae to adults, resulting in the formation of abnormal insects which have not attained their full adult growth and which may also be non-viable or sterile. Such treatment ultimately leads, at least indirectly, to the destruction or partial elimination of a pest population.

Compounds having a similar structure, but containing no cycloalkyl groups are contained in U.S. Pat. No. 3,846,466.

In one aspect, the present invention relates to compounds useful in controlling certain insects, particularly in impeding the metamorphosis of such insects. In another aspect, this invention relates to a process for selectively controlling insects using said compounds.

In general, the compounds of this invention can be prepared by reacting a substituted 1,2-ethanediamine with an alkyl chlorothioformate in the presence of base, according to the reaction:

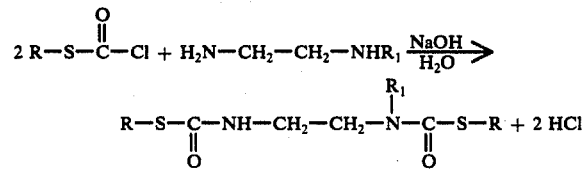

in which R and $R_1$ are as defined above. Preferably, the reaction is carried out in a solvent such as water, with stirring, by slowly adding the alkyl chlorothioformate to the diamine in the presence of an acid acceptor such as sodium hydroxide, generally at a temperature of about 0° C, followed by stirring at room temperature to complete the reaction, which is exothermic. The reaction product is recovered by conventional techniques such as extracting with methylene chloride, washing the solvent phase with water and drying with anhydrous magnesium sulfate. Finally, the solvent is filtered and removed by vacuum stripping. Preferably, the reaction is carried out using the proportions as above; that is, two moles of alkyl chlorothioformate per mole of amine, although a slight excess of a reactant can be used.

For example, N-ethyl-N,N'-bis(cyclopentylthiolcarbonyl)ethylenediamine (Compound 1 in Table I below) was prepared as follows:

2.2 g (0.025 mole) N-ethyl-ethylenediamine, 25 ml of water and 2.5 g (0.05 mole + 25% excess) NaOH were mixed together and stirred. There was added dropwise 8.2 g (0.05 mole) cyclopentyl chlorothioformate and the resulting mixture stirred for one hour. The product was extracted with methylene chloride, washed with water, dried and stripped. The yield was 6.1 g (72% of theoretical) of compound 1, m.p. 68°–72° C.

The following is a table of compounds representative of the invention which may be prepared in accordance with the general procedure described hereinabove. The compound numbers are assigned to each compound and are used throughout the remainder of the specification.

TABLE I

| Compound No. | R | $R_1$ | m.p., ° C |
|---|---|---|---|
| 1 | cyclopentyl | $C_2H_5$ | 68–72 |
| 2 | cyclohexyl | $C_2H_5$ | 65–68 |
| 3 | cyclopentyl | $CH_3$ | 91–92 |

INSECTICIDAL EVALUATION TEST

The degree of activity of a candidate compound to hinder or impede the metamorphosis of insects is measured by treating the penultimate larval stage of representative insects with the compound and examining them after their last molt toward the adult form for retention of immature features. Tests were conducted according to the following procedures.

a. Yellow mealworm (*Tenebrio molitor*, L.) larvae are maintained at 28° C and 40% humidity. The test compounds are diluted in acetone and topically applied in 1 μl. drops to the abdomen of pupae which are less than 24 hours old. The treated pupae are incubated for 7 days at 28° C and 50% humidity until adults emerge (usually within 6 to 8 days). Emerged adults are graded as positive, negative or dead. Positive responses include abnormalities such as retention or urogomphi, gin traps, pupal cuticle, or the existence of adult-larval intermediates. Testing is done in decreasing rates starting from 10 μg/pupa. Table II below shows the dose of the test compound per pupa which resulted in positive responses or abnormalities in approximately 50% of the emerged adults, indicated as $ED_{50}$.

b. Housefly larvae (*Musca domestica*, L.) — The test chemicals are diluted in acetone and topically applied in 1 μl. drops to pre-pupal housefly larvae about 4 days old, maintained at temperatures of about 27° C. A separate group of untreated larvae are similarly maintained as a control. The treated larvae and control are then placed in 55×17mm glass Petri dishes with a filter paper disc covering the bottom. The larvae are then covered with a thin layer of slightly moist soil and stored at the same temperature until all control larvae have pupated and emerged as adults (about 5 days). Active compounds are determined as those which prevent the emergence of adults from the pupal cases. Tests are conducted at rates of from 10 μg/larva downwards. Table II lists the effective dose ($ED_{50}$) at which 50% of the flies fail to emerge.

c. Southern house mosquito (*Culex pipiens quinquefasciatus*, Say) — Tests are conducted on late 4th-instar larvae of the above mosquito (about 6 days old). Ten larvae are placed in a six-ounce wax paper cup containing 100 mls of an aqueous solution of the test chemical. A separate group of untreated larvae is similarly maintained, as a control. The cups are covered with black tulle cloth and stored at 21° C for approximately one week during which time the larvae in the control group will pupate and emerge as adult mosquitos. Positive responses correspond to larvae which either pupate and die before the adults emerge or in which the larvae metamorphose to the adults but the adults die during the emerging process. The compounds are tested in concentrations ranging from 1 ppm downwards. Table II shows the effective concentration ($ED_{50}$) of the test compounds at which approximately 50% of the larvae are positively affected.

TABLE II

| Compound No. | T. molitor ($\mu$g/pupa) | Approx. $ED_{50}$ C. pipiens(ppm) | M. domestica ($\mu$g/pupa) |
|---|---|---|---|
| 1 | 0.0015 | 0.2 | >10 |
| 2 | 0.3 | >1 | >10 |
| 3 | 0.002 | 0.08 | >10 |

The compounds of this invention are generally embodied into a form suitable for convenient application. For example, the compounds can be embodied into pesticidal compositions which are provided in the form of emulsions, suspensions, solutions, dusts, and aerosol sprays. In general, such compositions will contain, in addition to the active compound, the adjuvants which are normally found in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface-active agents; talc; pyrophyllite; diatomite; gypsum; clays; propellants, etc. If desired, however, the active compounds can be applied directly to feedstuffs, seeds, etc., upon which the pests feed. When applied in such a manner, it will be advantageous to use a compound which is not volatile.

The compounds can also be combined with baits in a conventional manner.

The precise manner in which the pesticide compositions of this invention are used in any particular instance will be readily apparent to a person skilled in the art. Generally, the active pesticide compound will be embodied in the form of a liquid composition, for example, an emulsion, suspension, or aerosol spray. While the concentration of the active pesticide in the present compositions can vary within rather wide limits, ordinarily the pesticide compound will comprise between about 0.01 and about 50 percent by weight of the composition.

What is claimed is:

1. A method for selectively impeding the metamorphosis of insects comprising applying to the insect at its larval stage, a metamorphosis-inhibiting effective amount of a compound having the formula

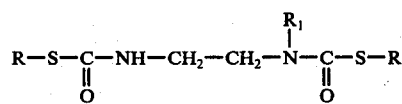

wherein R is cycloalkyl having from 3 to 7 carbon atoms, and $R_1$ is lower alkyl.

2. A method according to claim 1 wherein $R_1$ is lower alkyl having from 1 to 4 carbon atoms.

3. A method according to claim 1 wherein R is cyclopentyl.

4. A method according to claim 3 wherein $R_1$ is methyl.

5. A method according to claim 3 wherein $R_1$ is ethyl.

6. A composition effective in selectively impeding the metamorphosis of insects comprising: (a) a metamorphosis-inhibiting effective amount of a compound having the formula

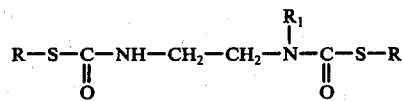

wherein R is cycloalkyl having from 3 to 7 carbon atoms, and $R_1$ is lower alkyl; and, (b) an inert carrier.

* * * * *